(12) United States Patent
Hirose (10) Patent No.: US 8,651,662 B2
(45) Date of Patent: Feb. 18, 2014

(54) OPTICAL TOMOGRAPHIC IMAGING APPARATUS AND IMAGING METHOD FOR OPTICAL TOMOGRAPHIC IMAGE

(75) Inventor: Futoshi Hirose, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 265 days.

(21) Appl. No.: 13/131,108

(22) PCT Filed: Dec. 16, 2009

(86) PCT No.: PCT/JP2009/071355
§ 371 (c)(1),
(2), (4) Date: May 25, 2011

(87) PCT Pub. No.: WO2010/074098
PCT Pub. Date: Jul. 1, 2010

(65) Prior Publication Data
US 2011/0234975 A1 Sep. 29, 2011

(30) Foreign Application Priority Data
Dec. 26, 2008 (JP) ................. 2008-331805

(51) Int. Cl.
*A61B 3/14* (2006.01)
*A61B 3/12* (2006.01)
*G01B 9/02* (2006.01)

(52) U.S. Cl.
CPC ... *A61B 3/12* (2013.01); *A61B 3/14* (2013.01); *G01B 9/02* (2013.01)
USPC ............ 351/206; 351/205; 351/246; 356/496

(58) Field of Classification Search
CPC ............... A61B 3/12; A61B 3/14; G01B 9/02
USPC .......... 351/205, 206, 210, 221, 246; 356/479, 356/496, 497; 382/154
See application file for complete search history.

(56) References Cited

U.S. PATENT DOCUMENTS 7,744,221 B2   6/2010  Wei et al.
7,933,024 B2   4/2011  Hirose
(Continued)

FOREIGN PATENT DOCUMENTS

JP   2003-052632 A   2/2003
JP   2008-528954 A   7/2008
(Continued)

OTHER PUBLICATIONS

International Preliminary Report on Patentability dated Jun. 29, 2011, in counterpart International Application No. PCT/JP2009/071355.

(Continued)

*Primary Examiner* — Huy K Mai
(74) *Attorney, Agent, or Firm* — Fitzpatrick, Cella, Harper & Scinto (57) ABSTRACT

Provided are an optical tomographic imaging apparatus and an imaging method for an optical tomographic image, in which high measurement sensitivity and high lateral resolution of a specific portion of an object may be obtained with a simple structure. The optical tomographic imaging apparatus of a Fourier-domain method includes: an optical path length adjustment portion for adjusting an optical path length of the reference beam; a position adjustment portion for adjusting a position of a focusing device for focusing the measuring beam onto the object; and a drive control portion for controlling drive of the optical path length adjustment portion and the position adjustment portion. The drive control portion is controlled based on information from a layer constituting a cross section from cross section information that is obtained in advance for a portion to be imaged of the object.

16 Claims, 8 Drawing Sheets

(56) References Cited

U.S. PATENT DOCUMENTS

| | | | |
|---|---|---|---|
| 8,115,935 | B2 | 2/2012 | Everett et al. |
| 2006/0164653 | A1 | 7/2006 | Everett et al. |
| 2006/0187462 | A1* | 8/2006 | Srinivasan et al. ............ 356/479 |
| 2007/0086011 | A1 | 4/2007 | Toida |
| 2007/0195269 | A1 | 8/2007 | Wei et al. |
| 2009/0091766 | A1 | 4/2009 | Hirose |
| 2009/0285354 | A1 | 11/2009 | Hirose et al. |
| 2010/0002241 | A1 | 1/2010 | Hirose |
| 2010/0007894 | A1 | 1/2010 | Suehira |
| 2010/0027019 | A1 | 2/2010 | Suehira |
| 2010/0103374 | A1 | 4/2010 | Hirose et al. |
| 2010/0166293 | A1* | 7/2010 | Sugita et al. .................. 382/154 |
| 2010/0245838 | A1 | 9/2010 | Everett et al. |
| 2010/0321700 | A1 | 12/2010 | Hirose et al. |
| 2011/0273668 | A1 | 11/2011 | Hirose |
| 2012/0140175 | A1 | 6/2012 | Everett et al. |

FOREIGN PATENT DOCUMENTS

| | | |
|---|---|---|
| JP | 2009-523563 A | 6/2009 |
| WO | 2006/077107 A1 | 7/2006 |
| WO | 2007/084748 A2 | 7/2007 |
| WO | 2008129863 A1 | 10/2008 |
| WO | 2008142823 A1 | 11/2008 |

OTHER PUBLICATIONS

International Search Report mailed Apr. 6, 2010, and discussed in a Written Opinion of the International Searching Authority completed Mar. 24, 2010, in International Application No. PCT/JP2009/071355.

Tomasz Bajraszewski et al., Improved spectral optical coherence tomography using optical frequency comb, Optics Express, vol. 16, No. 6, Mar. 17, 2008, pp. 4163-4176.

* cited by examiner

OPTICAL TOMOGRAPHIC IMAGING APPARATUS AND IMAGING METHOD FOR OPTICAL TOMOGRAPHIC IMAGE

TECHNICAL FIELD

The present invention relates to an optical tomographic imaging apparatus and an imaging method for an optical tomographic image, and more particularly, to an optical tomographic imaging apparatus and an imaging method for an optical tomographic image that are used for ophthalmological care or the like.

BACKGROUND ART

Currently, there are various types of ophthalmological apparatuses using an optical apparatus.

For instance, as an optical apparatus for observing an eye, there are used various apparatuses such as an anterior eye part imaging apparatus, a fundus camera, a scanning laser ophthalmoscope (SLO), and the like.

In particular, an optical tomographic imaging apparatus that performs an optical coherence tomography (OCT) utilizing interference phenomenon of multi-wavelength light is an apparatus capable of obtaining a tomographic image of a sample with high resolution.

This apparatus is becoming an indispensable apparatus as an ophthalmological apparatus for a specialist of retina in an outpatient field. Hereinafter, this apparatus is referred to as an OCT apparatus.

In the above-mentioned OCT apparatus, a measuring beam that is low coherence light is projected to a sample, and backscattered light from the sample may be measured with high sensitivity by using an interferometer.

In addition, the OCT apparatus may obtain a tomographic image with high resolution by scanning the sample with the measuring beam.

Therefore, the OCT apparatus may also take a tomographic image of a retina in a fundus of an eye to be inspected with high resolution, and thus is used widely for ophthalmological diagnosis of retina or the like.

In recent years, the OCT apparatus for the ophthalmological use is changing from a conventional time-domain method to a Fourier-domain method that may enable faster imaging.

In the case of high speed imaging, it is possible to prevent blurring or missing of an image due to an ocular movement such as small involuntary eye movements.

Compared with the time-domain method that obtains information for each specific depth in the eye to be inspected, the Fourier-domain method obtains information in the depth direction collectively, and hence high speed imaging may be performed.

However, in the case of the Fourier-domain method, it is known that the collective obtaining of information in the depth direction places some limitations on imaging.

In this situation, U.S. Patent Application Publication No. 2007/0086011 proposes a method of obtaining an optical tomographic image using a Fourier-domain OCT apparatus, which deals with the problem that lateral resolution of a tomographic image is limited by a depth of an object.

U.S. Patent Application Publication No. 2007/0086011 discloses an apparatus that is configured to extract information within an in-focus range of the measuring beam of the OCT apparatus so as to prevent deterioration in the lateral resolution.

On the other hand, "Improved spectral optical coherence tomography using optical frequency comb," Opt. Express 16, 4163-4176 (2008) describes that measurement sensitivity in imaging a tomographic image depends on a position of a reference mirror in a Fourier-domain OCT apparatus. In other words, it is described that the measurement sensitivity is limited by a depth of an object.

As described above, the Fourier-domain OCT apparatus has a problem that the lateral resolution and the measurement sensitivity of the tomographic image are limited by the depth of the object.

U.S. Patent Application Publication No. 2007/0086011, as described above, discloses extraction of a high lateral resolution part from the tomographic image in obtaining a high lateral resolution tomographic image by using the Fourier-domain OCT apparatus.

However, U.S. Patent Application Publication No. 2007/0086011 does not mention the case where the object such as a fundus moves, or does not pay attention to a specific layer.

In addition, "Improved spectral optical coherence tomography using optical frequency comb," Opt. Express 16, 4163-4176 (2008) discloses a structure of the Fourier-domain OCT apparatus in which the measurement sensitivity is hardly limited by a depth of an object, but it is complicated in its structure because a special light source called an optical frequency comb is used therein.

DISCLOSURE OF THE INVENTION

In view of the above-mentioned problem, it is an object of the present invention to provide an optical tomographic imaging apparatus and an imaging method for an optical tomographic image in structuring a Fourier-domain OCT apparatus, in which high measurement sensitivity and high lateral resolution at a predetermined part of the object may be obtained with a simple structure.

In addition, it is another object of the present invention to provide an optical tomographic imaging apparatus and an imaging method for an optical tomographic image, in which, when the object is a fundus, high measurement sensitivity and high lateral resolution of a specific layer of its retina may be obtained with a simple structure.

The present invention provides an optical tomographic imaging apparatus and an imaging method for an optical tomographic image, which have the following structures.

The present invention provides an optical tomographic imaging apparatus of a Fourier-domain method that is configured to:

split a light beam from a light source into a measuring beam and a reference beam;

direct the measuring beam to an object and direct the reference beam to a reference mirror; and use a return beam of the measuring beam reflected or scattered by the object and a reference beam reflected by the reference mirror to take a tomographic image of the object, the optical tomographic imaging apparatus including:

an optical path length adjustment portion for adjusting an optical path length of the reference beam;

a position adjustment portion for adjusting a position of a focusing device for focusing the measuring beam onto the object; and a drive control portion for controlling drive of the optical path length adjustment portion and the position adjustment portion, in which the drive control portion is controlled based on information from a layer constituting a cross section from cross section information that is obtained in advance for a portion to be imaged of the object.

Further, the present invention provides an imaging method for an optical tomographic image by a Fourier-domain method in which:

a light beam from a light source is split into a measuring beam and a reference beam;

the measuring beam is directed to an object and the reference beam is directed to a reference mirror; and a return beam of the measuring beam reflected or scattered by the object and a reference beam reflected by the reference mirror are used to take a tomographic image of the object, the imaging method for an optical tomographic image including:

imaging the tomographic image of a portion to be imaged of the object for obtaining information about the portion to be imaged in advance;

controlling a drive control portion for controlling drive of a position adjustment portion for adjusting a position of a focusing device for focusing the measuring beam onto the object and an optical path length adjustment portion for adjusting an optical path length of the reference beam, based on information about a layer constituting the taken tomographic image; and imaging the tomographic image of the object.

The OCT apparatus of the present invention includes the optical path length adjustment portion, the position adjustment portion, and the drive control portion for controlling the drive of the optical path length adjustment portion and the position adjustment portion. The drive control portion is controlled based on the information about the layer constituting the cross section among the cross section information obtained in advance for the portion to be imaged of the object.

Thus, the optical path length adjustment portion and the position adjustment portion may be controlled optimally based on the information obtained in advance about the layer constituting the cross section. Therefore, it is possible to provide the optical tomographic imaging apparatus and the imaging method for an optical tomographic image, which may obtain high measurement sensitivity and high lateral resolution of a specific portion of the object with a simple structure.

In addition, in a case that the object is a fundus, it is possible to provide the optical tomographic imaging apparatus and the imaging method for an optical tomographic image, which may obtain high measurement sensitivity and high lateral resolution of a specific layer of its retina with a simple structure.

Further features of the present invention will become apparent from the following description of exemplary embodiments with reference to the attached drawings.

BEST MODE FOR CARRYING OUT THE INVENTION

Hereinafter, an embodiment mode of the present invention is described with reference to the attached drawings.

In this embodiment mode, the above-mentioned structure of the present invention is applied to thereby structure, for example, the following optical tomographic imaging apparatus and imaging method for an optical tomographic image.

Figure 1:
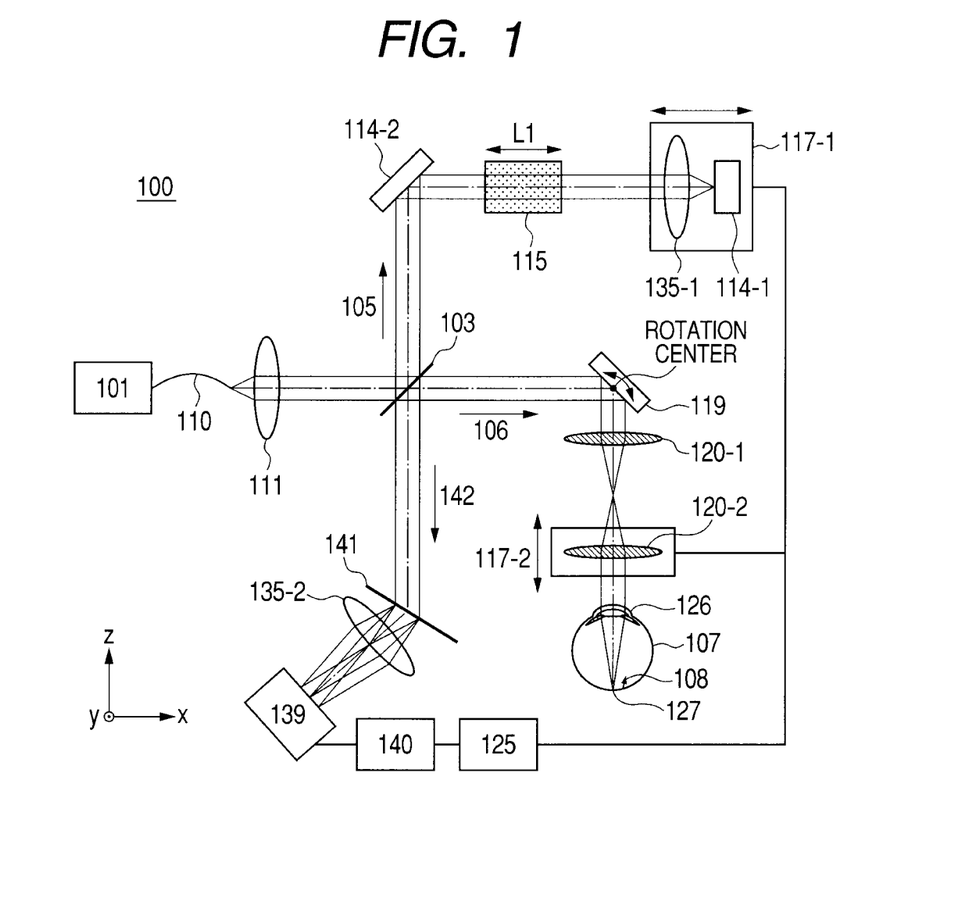
FIG. 1 is a diagram illustrating a structure of an optical system of an OCT apparatus according to Embodiment 1 of the present invention.

(1) As illustrated in FIG. 1, the optical tomographic imaging apparatus of this embodiment mode splits a light beam from a light source 101, into a measuring beam 106 and a reference beam 105, directs the measuring beam to an object (eye 107 to be inspected) and directs the reference beam to a reference mirror 114-1, and uses a return beam of the measuring beam reflected or scattered by the object and a reference beam reflected by the reference mirror to thereby take a tomographic image of the object. In this manner, the optical tomographic imaging apparatus of a Fourier-domain method is structured.

In this case, the present invention has the following structure for solving the above-mentioned problem.

The structure of the present invention includes an optical path length adjustment portion 117-1 for adjusting an optical path length of the reference beam, a position adjustment portion 117-2 for adjusting a position of a focusing device for focusing the measuring beam onto the object, and a drive control portion 125 for controlling drive of the optical path length adjustment portion 117-1 and the position adjustment portion 117-2.

Further, the drive control portion 125 is controlled based on information from a layer constituting a cross section from cross section information obtained in advance for a portion to be imaged of the object.

In other words, provided is the drive control portion 125, which controls the optical path length adjustment portion and the position adjustment portion based on the information obtained in advance for the portion to be imaged of the object.

With this structure, measurement sensitivity of a specific portion of the object may be optimally controlled. As a result, a tomographic image with high contrast of the specific portion may be obtained.

In addition, a beam diameter of the measuring beam in a specific portion of the object may be optimally controlled. As a result, a tomographic image with high lateral resolution of the specific portion may be obtained. And as a result, a tomographic image with high measurement sensitivity and high lateral resolution of the specific portion may be obtained.

(2) The above-mentioned description "based on information from a layer constituting a cross section from cross section information obtained in advance for a portion to be imaged" in the structure of the optical tomographic imaging apparatus of this embodiment is concerned about at least one layer of various types of layers constituting a human eyeball, for example, and means to perform optimal measurement in accordance with different curvatures of layers depending on individual objects. In other words, optimal measurement in which the curvatures of layers constituting a human eyeball are considered may be performed based on information from a layer constituting a cross section from cross section information.

In view of considering the curvatures of layers, it is necessary to obtain cross section information of the portion to be imaged once in advance.

In the optical tomographic imaging apparatus of the present invention, the cross section information includes information about two or more cross sections.

In this case, the two or more cross sections may be parallel to each other, but more desirably intersect each other because the curvatures may accurately be reflected on the measurement.

Further, according to the present invention, the drive control portion is controlled based on information about a surface including two or more layers constituting the two or more cross sections among the information about two or more cross sections.

For instance, the used information may be information about a surface (three-dimensional curved surface) calculated from layers (reference numerals 144 and 145 in FIG. 3A) constituting two or more tomographic images that substantially orthogonally cross each other in the portion to be imaged.

The drive control portion may be constituted of various types of computers, a signal processing device (information processing device or video information processing device), or the like. The drive control portion controls the drive of the optical path length adjustment portion and the position adjustment portion of the focusing device along one layer of the cross section information.

Here, when information about a surface is calculated from a layer constituting the cross section, in a case that a human eyeball is the object, for example, surface information may be calculated from information about one layer constituting the cross section by using a computer or the like, and it is also possible to accumulate data of the human eyeball in the computer in advance, to thereby calculate the surface information using the accumulated data and the obtained information about the layer constituting the cross section.

In the following description, an example in which the optical path length adjustment portion and the position control portion of the focusing device are driven and controlled with reference to a calculated three-dimensional curved surface is described. However, the reference is not necessarily the curved surface, and one layer of the cross section may be the reference.

(3) In addition, the optical tomographic imaging apparatus of this embodiment mode may include a notification device for notifying that information about a layer (e.g., three-dimensional curved surface) is calculated.

With this structure, the calculated layer information (e.g., three-dimensional curved surface (reference numeral 150 in FIG. 3D)) may be confirmed. In addition, before imaging a tomographic image, the curved surface based on the calculation layer information may be confirmed, with the result that the tomographic image may be obtained with higher accuracy.

(4) In addition, the optical tomographic imaging apparatus of this embodiment mode may inspect a specific layer of a retina when the object is an eye to be inspected.

Thus, a tomographic image with high measurement sensitivity and high lateral resolution may be obtained for a predetermined portion of a retina tissue.

(5) In addition, the optical tomographic imaging apparatus of this embodiment mode may inspect a retinal pigment epithelial layer as the specific layer of the retina.

In this way, if the retinal pigment epithelial layer is selected as the specific layer of the retina, the specific layer of the retina may be recognized easily because the retinal pigment epithelial layer has high reflectivity of the measuring beam.

As a result, the imaging surface may be calculated accurately. And as a result, a tomographic image with high measurement sensitivity and high lateral resolution may be obtained.

(6) In addition, the optical tomographic imaging apparatus of this embodiment mode may inspect a retinal nerve fiber layer as the specific layer of the retina.

In this way, if the retinal nerve fiber layer is selected as the specific layer of the retina, the specific layer of the retina may be recognized easily because the retinal nerve fiber layer has high reflectivity of the measuring beam.

As a result, the imaging surface may be calculated accurately. And as a result, a tomographic image with high measurement sensitivity and high lateral resolution may be obtained.

(7) In addition, the optical tomographic imaging apparatus of this embodiment mode may include a fundus camera main body portion of the optical tomographic imaging apparatus for imaging a tomographic image of the fundus of the eye to be inspected, and a camera portion for imaging a surface image of the fundus of the eye to be inspected.

Thus, both the functions of the fundus camera and the OCT apparatus may be realized by a single apparatus.

Therefore, it is possible to realize an OCT apparatus with high efficiency in space use and high profitability.

(8) In addition, the optical tomographic imaging apparatus of this embodiment mode may have a structure in which the fundus camera main body portion and the camera portion for imaging the surface image of the fundus may be connected via an adapter.

Thus, it is possible to realize the function of the OCT apparatus by using an existing fundus camera.

(9) This embodiment mode also provides an imaging method for an optical tomographic image by a Fourier-domain method in which: a light beam from a light source is split into a measuring beam and a reference beam; the measuring beam is directed to an object and the reference beam is directed to a reference mirror; and a return beam of the measuring beam reflected or scattered by the object and a reference beam reflected by the reference mirror are used to take a tomographic image of the object, the imaging method for an optical tomographic image including: imaging the tomographic image of a portion to be imaged of the object for obtaining information about the portion to be imaged in advance; controlling a drive control portion for controlling drive of a position adjustment portion for adjusting a position of a focusing device for focusing the measuring beam onto the object and an optical path length adjustment portion for adjusting an optical path length of the reference beam, based on information about a layer constituting the taken tomographic image; and imaging the tomographic image of the object.

The above-mentioned method of this embodiment mode includes the following method.

The method includes: a first step of imaging two or more tomographic images that cross each other (e.g., are substantially orthogonal to each other) of the portion to be imaged for obtaining information about the portion to be imaged of the object in advance; a second step of processing the two or more taken tomographic images; a third step of calculating a three-dimensional plane by using the two or more processed tomographic images; and a fourth step of using the drive control portion for driving and controlling the position adjustment portion for adjusting a position of the focusing device for focusing the measuring beam onto the object, and the optical path length adjustment portion for adjusting the optical path length of the reference beam, so as to control the position adjustment portion for focusing the measuring beam on the three-dimensional plane and so as to control the optical path length adjustment portion for moving the reference mirror to a position corresponding to the imaging surface, with the result that a three-dimensional tomographic image of the object may be taken.

Thus, the tomographic image with high measurement sensitivity and high lateral resolution may effectively be obtained.

(10) In addition, the imaging method for an optical tomographic image according to this embodiment mode may automatically perform at least one of the first to the fourth steps.

Thus, a tomographic image with high measurement sensitivity and high lateral resolution may efficiently be obtained.

Embodiment

Next, embodiments of the present invention are described.

Embodiment 1

In Embodiment 1, an optical tomographic imaging apparatus (OCT apparatus) to which the present invention is applied is described.

In this embodiment, in particular, an apparatus for imaging a tomographic image (OCT image) of an eye to be inspected is described.

The OCT apparatus described in this embodiment is a Fourier-domain OCT apparatus (Fourier Domain OCT).

First, a general schematic structure of an optical system of an OCT apparatus according to this embodiment is described.

FIG. 1 is a diagram illustrating the general schematic structure of the optical system of the OCT apparatus according to this embodiment.

In FIG. 1, an OCT apparatus 100 includes a light source 101, a beam splitter 103, and a single mode fiber 110. Further, a reference beam is represented by 105, a measuring beam is represented by 106, a combined light beam is represented by 142, an eye to be inspected is represented by 107, and a return beam is represented by 108.

The OCT apparatus 100 further includes lenses 111, 120-1, 120-2, 135-1, and 135-2, mirrors 114-1 and 114-2, and a dispersion compensation glass 115. The OCT apparatus 100 further includes an electrical stage 117-1 constituting an optical path length adjustment portion for adjusting the optical path length of the reference beam, and an electrical stage 117-2 constituting a position adjustment portion for adjusting a focus position of a focusing device.

The OCT apparatus 100 further includes an XY scanner 119, and a personal computer 125 constituting a drive control portion for controlling the drive of the electrical stages 117-1 and 117-2. The personal computer 125 constitutes both the drive control portion and a control portion for performing an image processing and a signal processing, and further works as a display portion for displaying the tomographic image.

The eye 107 to be inspected has a cornea 126 and a retina 127. Further illustrated in FIG. 1 are a line camera 139, a frame grabber 140, and a transmission grating 141.

As illustrated in FIG. 1, the OCT apparatus 100 of this embodiment constitutes a Michelson interferometer as a whole.

In FIG. 1, the light beam emitted from the light source 101 is split by the beam splitter 103 into the reference beam 105 and the measuring beam 106.

The measuring beam 106 is reflected or scattered by the eye 107 to be inspected to be observed so as to become the return beam 108 and is combined with the reference beam 105 by the beam splitter 103.

After the reference beam 105 and the return beam 108 are combined, the transmission grating 141 performs spectral processing of the beams for each wavelength, and then each beam enters the line camera 139.

The line camera 139 converts light intensity at each position (wavelength) into voltage, and the tomographic image of the eye 107 to be inspected is formed by using the voltage signals.

Next, a periphery of the light source 101 is described.

The light source 101 is a super luminescent diode (SLD) that is a typical low coherence light source.

The wavelength is 830 nm, and the bandwidth is 50 nm. Here, the bandwidth is an important parameter because the bandwidth affects the resolution of the obtained tomographic image in the optical axis direction.

In addition, the light source of an SLD type is used in this embodiment, but an amplified spontaneous emission (ASE) type or the like may also be used as long as the light source may emit low coherence light.

In addition, concerning the wavelength of light, near-infrared light is suitable because the light is used for measuring an eye. Further, the wavelength affects the resolution of the obtained tomographic image in the lateral direction, so the wavelength is desirably as short as possible. Here, the wavelength is 830 nm. Depending on the measurement region to be observed, other wavelength may be selected.

The light beam emitted from the light source 101 is directed to the lens 111 through the single mode fiber 110 and is adjusted to be a parallel beam having a beam diameter of 1 mm.

Next, the optical path of the reference beam 105 is described.

The reference beam 105 split by the beam splitter 103 enters the mirror 114-2 and changes its direction, and is then condensed by the lens 135-1 onto the mirror 114-1 to be reflected and directed to the beam splitter 103 again.

Next, the reference beam 105 passes through the beam splitter 103 and is directed to the line camera 139. Here, the dispersion compensation glass 115 is disposed.

The dispersion compensation glass 115 compensates for the dispersion of the measuring beam 106 when the measuring beam 106 enters the eye 107 to be inspected and is reflected thereby, with respect to the reference beam 105.

Here, a typical value of a diameter of a Japanese average eyeball is assumed to be $L1=23$ mm.

Further, an electrical stage 117-1 may move in the direction indicated by the arrow, so that the optical path length of the reference beam 105 may be adjusted and controlled.

In addition, the electrical stage 117-1 may be controlled by the personal computer 125 at high speed, which is characteristic of the present invention.

Next, the optical path of the measuring beam 106 is described.

The measuring beam 106 split by the beam splitter 103 enters the mirror of the XY scanner 119.

In FIG. 1, for simple description, the XY scanner 119 is illustrated as a single mirror, but actually, two mirrors of an X scan mirror and a Y scan mirror are disposed closely to each other so as to raster-scan the retina 127 in the direction perpendicular to the optical axis.

In addition, the center of the measuring beam 106 is aligned with the rotation center of the mirror of the XY scanner 119.

The lenses 120-1 and 120-2 constitute the optical system for scanning the retina 127 and have a role of scanning the retina 127 with the measuring beam 106 with a fulcrum in a vicinity of the cornea 126.

Here, focal lengths of the lenses 120-1 and 120-2 are 50 mm each.

In addition, the electrical stage 117-2 may move in the direction indicated by the arrow in the diagram, so that a position of the accompanying lens 120-2 may be adjusted and controlled. By adjusting the position of the lens 120-2, the measuring beam 106 may be focused on a specific layer of the retina 127 of the eye 107 to be inspected for observation.

In addition, it is possible to support the case where the eye 107 to be inspected has a refractive error. When the measuring beam 106 enters the eye 107 to be inspected, the measuring beam 106 becomes the return beams 108 after being reflected or scattered by the retina 127, and then the return beams 108 are reflected by the beam splitter 103 to be directed to the line camera 139.

Here, the electrical stage 117-2 may be controlled by the personal computer 125 at high speed, and this is a characteristic structure of the OCT apparatus of this embodiment.

Next, a structure of a measurement system of the OCT apparatus according to this embodiment is described.

The OCT apparatus 100 may obtain a tomographic image (OCT image) constituted of intensity of the interference signal by the Michelson interferometer.

The measurement system is described below. The return beams 108 that is light reflected or scattered by the retina 127 is reflected by the beam splitter 103.

Here, it is adjusted so that the reference beam 105 and the return beams 108 are combined behind the beam splitter 103.

Further, the combined light beam 142 is spectrally processed for each wavelength by the transmission grating 141 and is condensed by the lens 135-2, and then the line camera 139 converts the light intensity for each position (wavelength) into a voltage.

Specifically, an interference pattern of the spectrum region on the wavelength axis is observed by the line camera 139.

The obtained voltage signals are converted into digital values by the frame grabber 140, and the digital values are supplied to the personal computer 125, which performs data processing so as to form the tomographic image.

Here, the line camera 139 has 1,024 pixels and may obtain intensity of the combined light beam 142 for each wavelength (1,024 splits).

Next, a method of obtaining the tomographic image by using the OCT apparatus is described.

The OCT apparatus 100 controls the XY scanner 119 and the line camera 139 obtains the interference pattern, with the result that the tomographic image of the retina 127 may be obtained (FIG. 1).

Here, the method of obtaining the tomographic image (surface parallel to the optical axis) of the retina 127 is described with reference to FIGS. 2A to 2C.

Figure 2A:
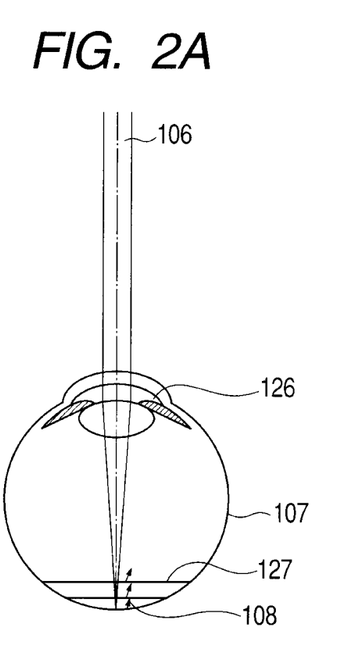
FIGS. 2A, 2B, and 2C are diagrams illustrating a method of obtaining a tomographic image by the OCT apparatus according to Embodiment 1 of the present invention.

FIG. 2A is a schematic diagram of the eye 107 to be inspected and illustrates a manner in which the eye 107 to be inspected is being observed by the OCT apparatus 100.

As illustrated in FIG. 2A, the measuring beam 106 passes through the cornea 126 and enters the retina 127. Then, the measuring beam 106 becomes the return beams 108 by being reflected or scattered at various positions and the return beams 108 reach the line camera 139 with time delays corresponding to the positions.

Here, the bandwidth of the light source 101 is wide, and a space coherence length is short. Therefore, if an optical path length for the reference beam is substantially equal to an optical path length for the measuring beam, the line camera 139 may detect the interference pattern.

In other words, the line camera 139 may obtain the interference pattern of the spectrum region on the wavelength axis.

Next, the interference pattern that is information on the wavelength axis is converted into an interference pattern on the optical frequency axis considering characteristics of the line camera 139 and the transmission grating 141.

Further, reverse Fourier transformation of the interference pattern of the converted optical frequency axis is performed, so that information on the depth direction may be obtained.

Figure 2B:
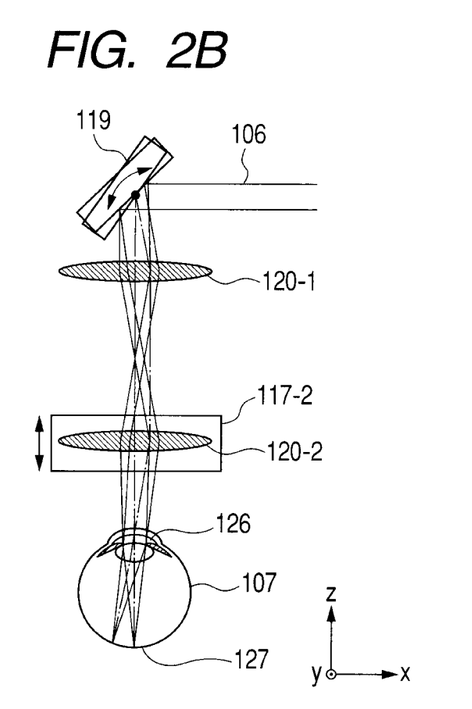
Figure 2C:
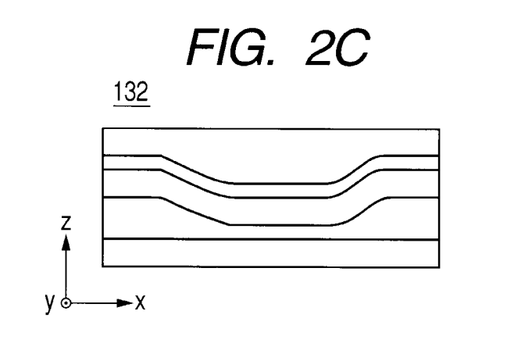

Further, as illustrated in FIG. 2B, the interference pattern is detected while the X axis of the XY scanner 119 is driven, with the result that the interference pattern at each position on the X axis may be obtained. In other words, information in the depth direction at each position on the X axis may be obtained.

As a result, two-dimensional distribution of intensity of the return beams 108 on the XZ plane, which is a tomographic image 132 (FIG. 2C), may be obtained.

Inherently, the tomographic image 132 is constituted of intensities of the return beams 108 arranged in an array as described above, and is displayed as a gray scale image corresponding to the intensities. In FIG. 2C, only boundaries of the obtained tomographic image are emphasized and displayed.

Next, the method of obtaining the three-dimensional image by using the OCT apparatus according to a first structural example of this embodiment is described.

Here, the case of noting the retinal pigment epithelial layer is described.

The electrical stage 117-1 controls a position of the mirror 114-1 as the reference mirror while the electrical stage 117-2 controls a position of the lens 120-2, with the result that the tomographic image of the retina 127 and the three-dimensional image constituted of a plurality of tomographic images may be obtained (FIG. 1).

FIGS. 3A to 3E are diagrams illustrating the method of obtaining the three-dimensional image by using the OCT apparatus according to the first structural example of this embodiment.

FIGS. 3A to 3E are diagrams illustrating a procedure of obtaining the three-dimensional image by the OCT apparatus 100 according to the first structural example.

Here, how to obtain the three-dimensional image of the retina 127 of the eye 107 to be inspected is described with reference to FIGS. 3A to 3E.

In particular, the case of measuring a vicinity of the retinal pigment epithelial layer (RPE layer) that is one of the tissues of the retina 127 with high measurement sensitivity and high lateral resolution is described.

Here, the case of noting the retinal pigment epithelial layer is described, but it is also possible to note other tissue for imaging the image thereof.

The method of obtaining the three-dimensional image according to the first structural example performs the following Steps 1 to 4 successively, for example. Alternatively, the obtaining method may return to any step if necessary.

Figure 4:
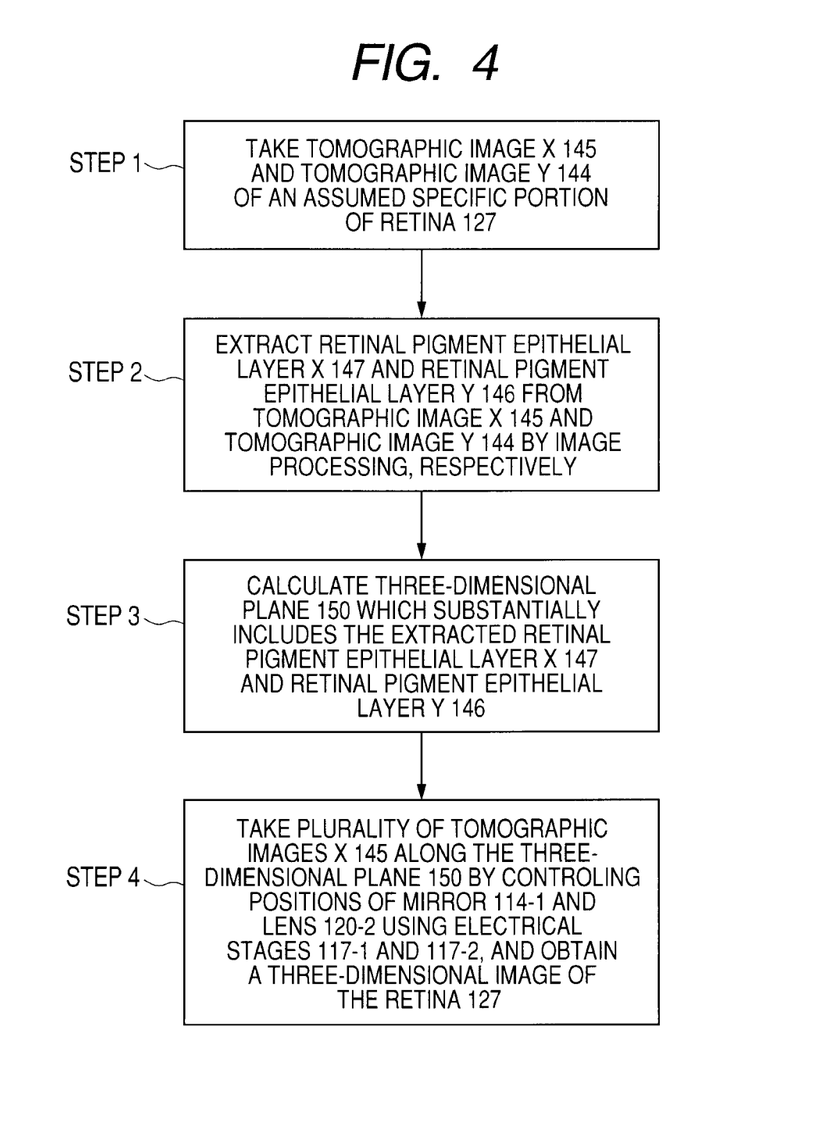
FIG. 4 is a diagram illustrating a process flow of Steps 1 to 4 of the method of obtaining the three-dimensional image by the OCT apparatus according to the first structural example of Embodiment 1 of the present invention.

In addition, computer or the like can be used, by which the following steps may automatically be performed. The process flow of Steps 1 to 4 is illustrated in FIG. 4.

Figure 3A:
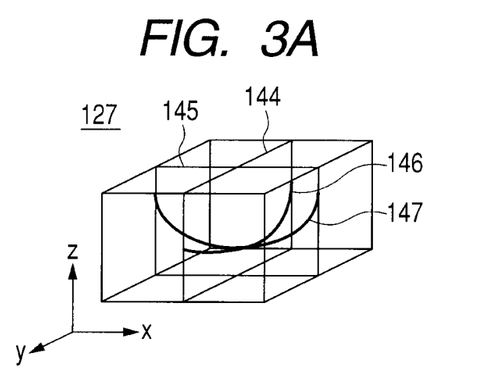
FIGS. 3A, 3B, 3C, 3D, and 3E are diagrams illustrating a method of obtaining a three-dimensional image by the OCT apparatus according to a first structural example of Embodiment 1 of the present invention.

(1) In Step 1, a specific portion of the retina 127 (here, retinal pigment epithelial layer) is assumed, and a tomographic image X 145 and a tomographic image Y 144 are taken (FIG. 3A).

Figure 3B:
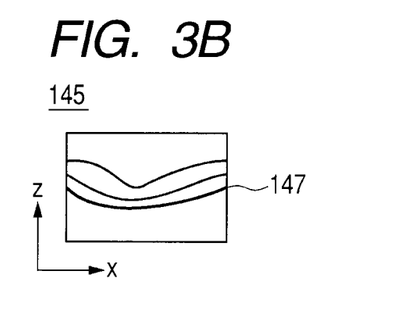
Figure 3C:
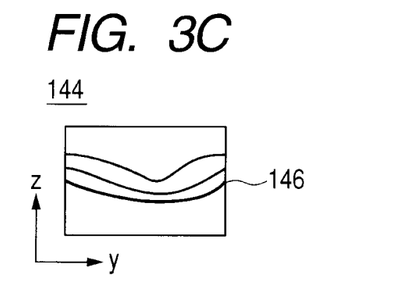

(2) In Step 2, a retinal pigment epithelial layer X 147 and a retinal pigment epithelial layer Y 146 are extracted from the obtained tomographic image X 145 and tomographic image Y 144 by image processing, respectively (FIGS. 3B and 3C).

Figure 3D:
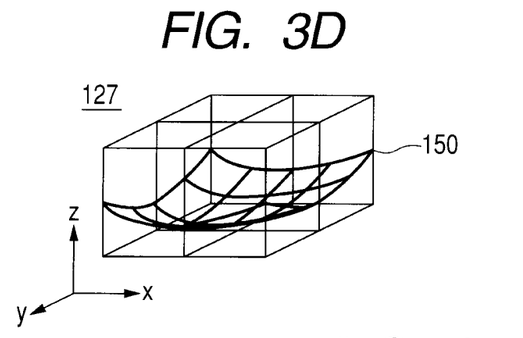

(3) In Step 3, the three-dimensional plane 150 which substantially includes the retinal pigment epithelial layer X 147 and the retinal pigment epithelial layer Y 146 extracted in Step 2 is predicted and calculated (FIG. 3D).

(4) In Step 4, the plurality of tomographic images X 145 are taken along the three-dimensional plane 150 calculated in Step 3 by controlling positions of the mirror 114-1 and the lens 120-2 (FIG. 1) using the electrical stages 117-1 and 117-2, and the three-dimensional image of the retina 127 may be obtained.

A specific control method in Step 4 will further be described.

The specific imaging method for the tomographic image in Step 4 is as follows.

Figure 3E:
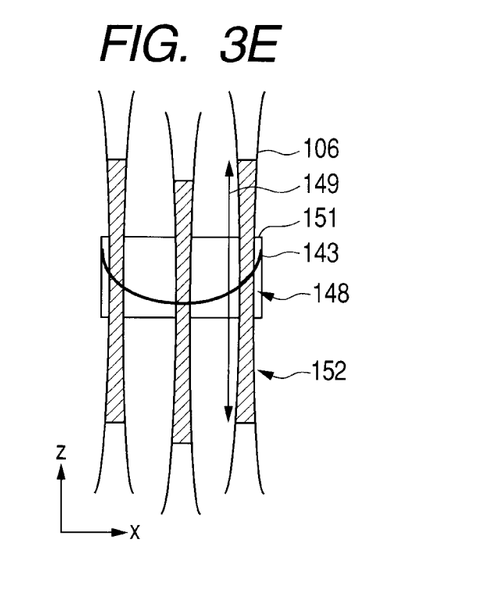

FIG. 3E is a diagram illustrating the control method and conceptually illustrates a manner in which the measuring beam 106 enters an imaging range 151 of the assumed XZ plane.

In FIG. 3E, a retinal pigment epithelial layer, a focal position at which the measuring beam 106 becomes thinnest, a focal depth, the imaging range, and a coherence gate indicating a position corresponding to an optical path length of the reference beam path are represented by 143, 148, 149, 151, and 152, respectively.

Here, the coherence gate 152 is controlled to be on a −Z side with respect to the focal position 148 within the range of the focal depth 149 and to be outside of the imaging range 151.

By controlling the coherence gate 152 to be outside of the imaging range, a mirror image that is a phenomenon unique to the Fourier-domain OCT apparatus does not occur.

In addition, the focal position 148 is controlled to be close to the retinal pigment epithelial layer 143, so that the lateral resolution in a vicinity of the retinal pigment epithelial layer 143 becomes optimal.

In addition, only three typical points for the position of the measuring beam 106 are indicated in FIG. 3E, but the above-mentioned control is performed for each position on the X axis.

By imaging as described above, the specific portion (here, retinal pigment epithelial layer 143) may be measured with high measurement sensitivity and high lateral resolution.

Here, the three-dimensional plane 150 is calculated in Step 3 and is used for the control in Step 4, but the three-dimensional plane 150 may be one obtained by another OCT apparatus or another ophthalmological apparatus.

Next, the method of obtaining the three-dimensional image by using the OCT apparatus according to a second structural example of this embodiment is described.

Here, the case of noting an optic disc is described. Similarly to the above-mentioned first structural example, the electrical stage 117-1 controls a position of the mirror 114-1 as the reference mirror while the electrical stage 117-2 controls a position of the lens 120-2. Thus, the tomographic image of the retina 127 and the three-dimensional image constituted of the plurality of tomographic images may be obtained (FIG. 1).

FIGS. 5A to 5E are diagrams illustrating the method of obtaining the three-dimensional image by using the OCT apparatus according to the second structural example.

FIGS. 5A to 5E are diagrams illustrating a procedure of obtaining the three-dimensional image by the OCT apparatus 100 according to the second structural example.

Here, how to obtain the three-dimensional image of the retina 127 of the eye 107 to be inspected is described with reference to FIGS. 5A to 5E.

In particular, the case of measuring a vicinity of the optic disc that is one of the tissues of the retina 127 with high measurement sensitivity and high lateral resolution is described.

In particular, a thickness of a nerve fiber layer of the optic disc of the retina 127 is noted.

Here, the case of noting the optic disc is described, but it is possible to note other tissue for imaging the image thereof.

The method of obtaining the three-dimensional image according to the second structural example performs the following Steps 1 to 4 successively, for example. Alternatively, the obtaining method may return to any step if necessary.

Figure 6:
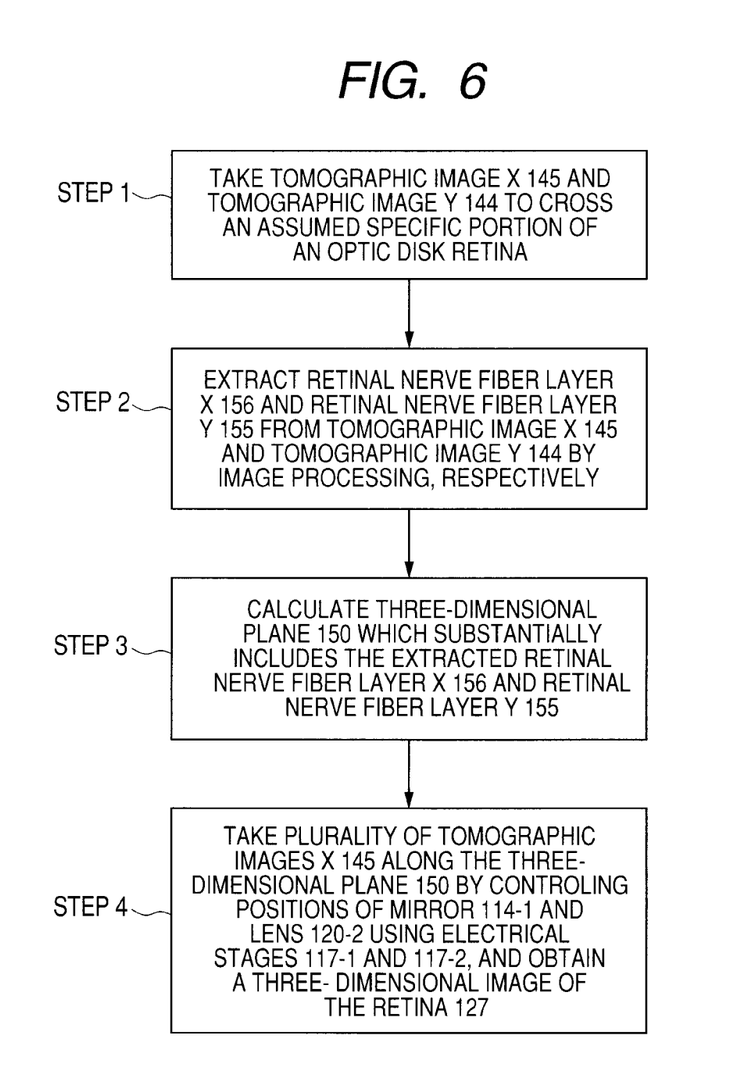
FIG. 6 is a diagram illustrating a process flow of Steps 1 to 4 of the method of obtaining the three-dimensional image by the OCT apparatus according to the second structural example of Embodiment 1 of the present invention.

In addition, a computer or the like can be used, by which the following steps may automatically be performed. The process flow of Steps 1 to 4 is illustrated in FIG. 6.

Figure 5A:
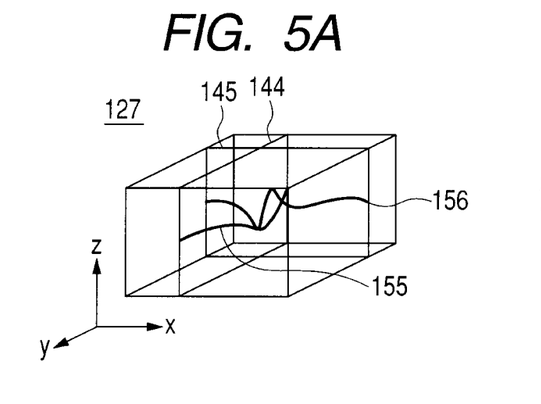
FIGS. 5A, 5B, 5C, 5D, and 5E are diagrams illustrating the method of obtaining a three-dimensional image by the OCT apparatus according to a second structural example of Embodiment 1 of the present invention.

(1) In Step 1, a specific portion of the retina 127 (here, optic disc) is assumed, and the tomographic image X 145 and the tomographic image Y 144 are taken so as to cross the specific portion (FIG. 5A).

Figure 5B:
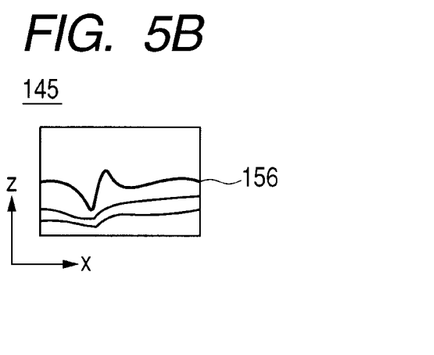
Figure 5C:
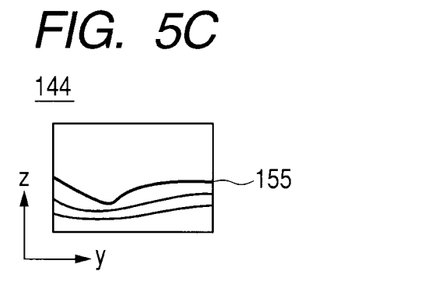
Figure 5D:
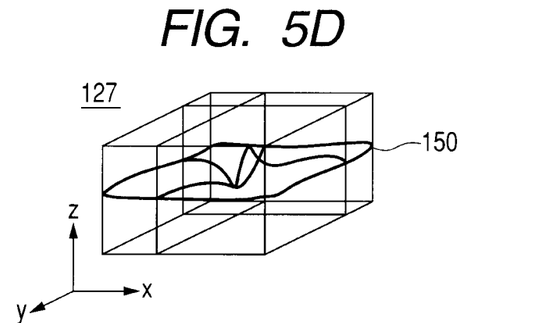

(2) In Step 2, a retinal nerve fiber layer X 156 and a retinal nerve fiber layer Y 155 are extracted from the obtained tomographic image X 145 and tomographic image Y 144 by image processing, respectively (FIGS. 5B and 5C).

(3) In Step 3, the three-dimensional plane 150 which substantially includes the retinal nerve fiber layer X 156 and the retinal nerve fiber layer Y 155 extracted in Step 2 (FIG. 5D) is predicted and calculated.

(4) In Step 4, the plurality of tomographic images X 145 are taken along the three-dimensional plane 150 calculated in Step 3 by controlling positions of the mirror 114-1 and the lens 120-2 (FIG. 1) using the electrical stages 117-1 and 117-2, and the three-dimensional image of the retina 127 may be obtained.

A specific control method in Step 4 will further be described.

The specific imaging method for the tomographic image in Step 4 is as follows.

Figure 5E:
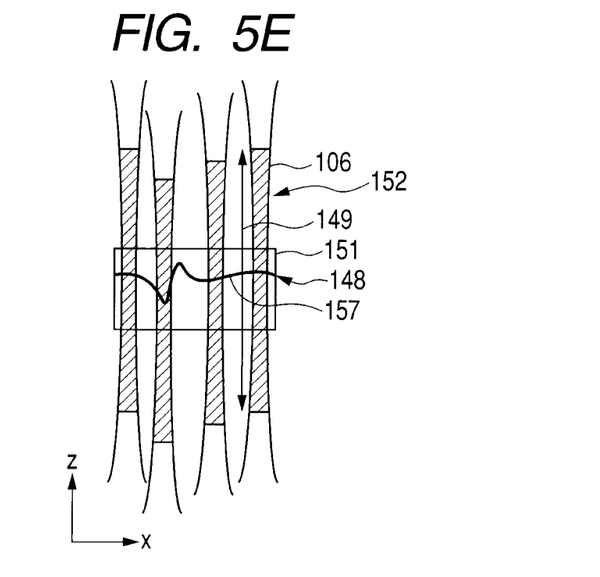

FIG. 5E is a diagram illustrating the control method and conceptually illustrates a manner in which the measuring beam 106 enters the imaging range 151 of the assumed XZ plane. In FIG. 5E, a retinal nerve fiber layer, the focal position at which the measuring beam 106 becomes thinnest, the focal depth, the imaging range, and the coherence gate indicating a position corresponding to an optical path length of the reference beam path are represented by 157, 148, 149, 151, and 152, respectively.

Here, the coherence gate 152 is controlled to be on a +Z side with respect to the focal position 148 within the range of the focal depth 149 and to be outside of the imaging range 151.

By controlling the coherence gate 152 to be outside of the imaging range, a mirror image that is a phenomenon unique to the Fourier-domain OCT apparatus does not occur.

In addition, the focal position 148 is controlled to be close to the retinal nerve fiber layer 157, so that the lateral resolution in a vicinity of the retinal nerve fiber layer 157 becomes optimal.

In addition, only four typical points for the position of the measuring beam 106 are indicated in FIG. 5E, but the above-mentioned control is performed for each position on the X axis.

By imaging as described above, the specific portion (here, retinal nerve fiber layer 157) may be measured with high measurement sensitivity and high lateral resolution.

Here, the three-dimensional plane 150 is calculated in Step 3 and is used for the control in Step 4, but the three-dimensional plane 150 may be one obtained by another OCT apparatus or another ophthalmological apparatus.

Embodiment 2

In Embodiment 2, an OCT apparatus to which the present invention applied is described.

In this embodiment, in particular, an apparatus for imaging a tomographic image (OCT image) and a fundus image (plane image) of an eye to be inspected are described. In this embodiment, an OCT apparatus including an OCT imaging portion connected to a fundus camera via an adapter is described. This embodiment describes an OCT apparatus with high space use efficiency and high profitability.

First, a general structure of the OCT apparatus including the adapter in this embodiment is described.

Figure 7:
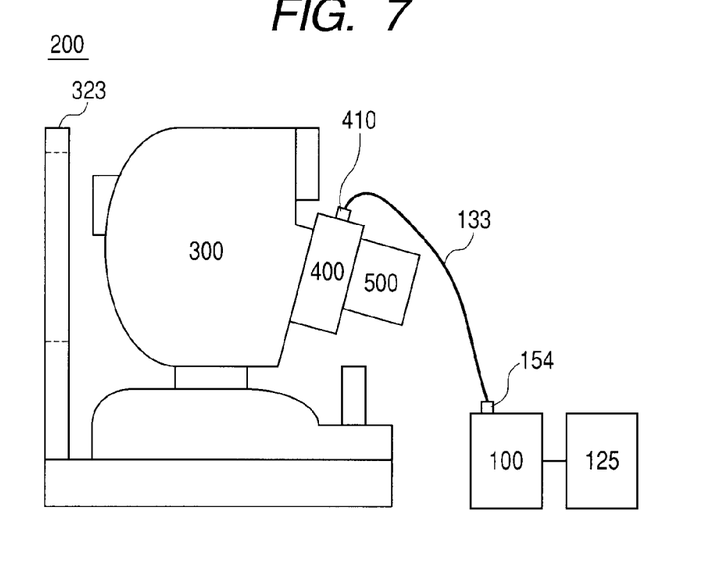
FIG. 7 is a diagram illustrating an entire structure of an OCT apparatus according to Embodiment 2 of the present invention.

FIG. 7 is a diagram illustrating the general structure of this embodiment.

In FIG. 7, an OCT apparatus 200 includes an OCT imaging portion 100 for imaging a tomographic image, a fundus camera main body portion 300, an adapter 400, a camera portion 500 for imaging a surface image of the fundus.

Here, the fundus camera main body portion 300, the adapter 400, and the camera portion 500 are optically connected to each other. Here, the fundus camera main body portion 300 and the adapter 400 are supported so as to be relatively movable.

Therefore, it is possible to roughly perform optical adjustment. In addition, the adapter 400 and the OCT imaging portion 100 are optically connected to each other via the single mode fiber 133.

The adapter 400 and the OCT imaging portion 100 have the connector 410 and the connector 154, respectively. Therefore, the adapter 400 and the OCT imaging portion 100 are easily attachable to and detachable from each other.

In addition, a chin support 323 fixes a chin and a forehead of a subject, so that the eye to be inspected is fixed in imaging the image. A personal computer 125 is used for creating and displaying the tomographic image.

Here, as the camera portion 500, a general-purpose digital single-lens reflex camera may be used, for example.

The camera portion 500 is connected to the adapter 400 or the fundus camera main body portion 300 via a general-purpose camera mount.

Next, a structure of an optical system of the OCT apparatus including the adapter according to this embodiment is described.

Figure 8:
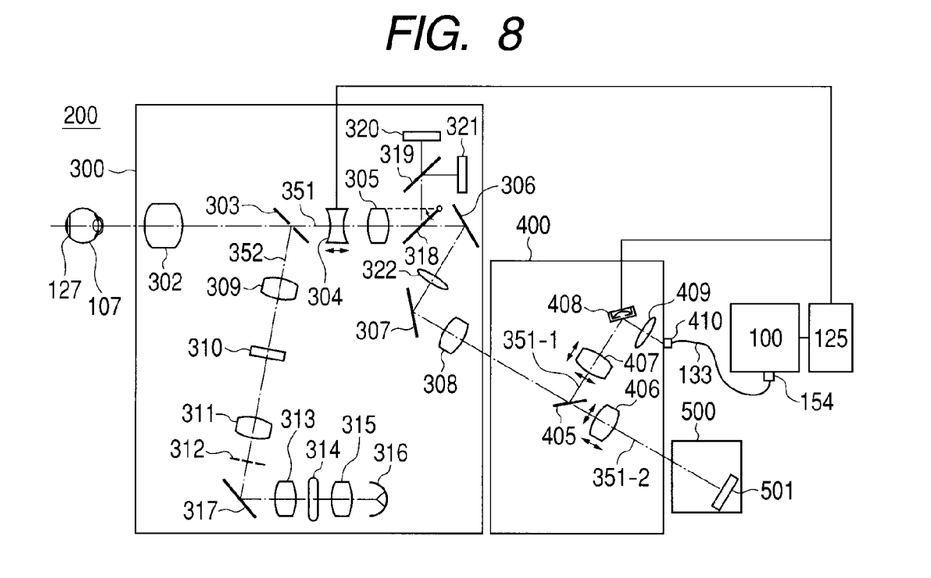
FIG. 8 is a diagram illustrating a structure of an optical system of the OCT apparatus according to Embodiment 2 of the present invention.

FIG. 8 is a diagram illustrating a structure of the optical system of the OCT apparatus.

In FIG. 8, the OCT apparatus 200 for measuring the eye 107 to be inspected includes a fundus camera main body portion 300, an adapter 400, a camera portion 500, and an OCT imaging portion 100.

The OCT apparatus 200 takes a tomographic image (OCT image) and a fundus image (plane image) of the retina 127 of the eye 107 to be inspected by using the OCT imaging portion 100 and the camera portion 500.

First, the fundus camera main body portion 300 is described. An objective lens 302 is disposed so as to be opposed to the eye 107 to be inspected, and on the optical axis thereof a perforated mirror 303 splits the optical path into an optical path 351 and an optical path 352.

The optical path 352 forms an illuminating optical system for illuminating the fundus of the eye 107 to be inspected. In a lower portion of the fundus camera main body portion 300, there are disposed a halogen lamp 316 that is used for positioning of the eye 107 to be inspected, and a strobe tube 314 that is used for imaging the fundus of the eye 107 to be inspected.

The fundus camera main body portion 300 further includes condenser lenses 313 and 315 and a mirror 317. Illuminating light from the halogen lamp 316 and the strobe tube 314 is shaped into a ring-like light flux by a ring slit 312 and is reflected by the perforated mirror 303 so as to illuminate the fundus of the eye 107 to be inspected. The fundus camera main body portion 300 further includes lenses 309 and 311 and an optical filter 310.

The optical path 351 constitutes an imaging optical system for imaging the tomographic image and the fundus image of the fundus of the eye 107 to be inspected.

A focus lens 304 and an imaging lens 305 are disposed on the right side of the perforated mirror 303.

Here, the focus lens 304 is supported so as to be movable in the optical axis direction, and the personal computer 125 may control the position thereof, which is characteristic of the present invention.

Next, the optical path 351 is directed to a fixation lamp 320 and an area sensor 321 via a quick return mirror 318.

Here, the quick return mirror 318 is designed to reflect and transmit a part of infrared light and to reflect visible light.

Because the quick return mirror 318 is designed to reflect and transmit a part of infrared light, the fixation lamp 320, the area sensor 321, and the OCT imaging portion 100 may be used simultaneously.

In addition, a dichroic mirror 319 is designed to direct visible light in the direction to the fixation lamp 320 and direct infrared light in the direction to the area sensor 321.

Next, the optical path 351 is directed to the adapter 400 via a mirror 306, a field lens 322, a mirror 307, and a relay lens 308.

Next, a structure of the optical system (adapter and camera portion) is described.

The largest function of the adapter 400 is to split the optical path 351 into an optical path 351-1 for imaging the tomographic image and an optical path 351-2 for imaging the fundus image via the dichroic mirror 405.

The adapter 400 further includes relay lenses 406 and 407, an XY scanner 408, and a collimate lens 409.

Here, the relay lenses 406 and 407 are supported in a movable manner, so that the optical axis may be adjusted between the optical paths 351-1 and 351-2 by a fine positional adjustment. In addition, in FIG. 8, the XY scanner 408 is illustrated as a single mirror for simple description, but actually two mirrors of an X scan mirror and a Y scan mirror are disposed to be close to each other so as to raster-scan the retina 127 in the direction perpendicular to the optical axis.

In addition, the XY scanner 408 is controlled by the personal computer 125. In addition, the optical axis of the optical path 351-1 is aligned with the rotation center of the two mirrors of the XY scanner 408.

In addition, a connector 410 is used for attaching the optical fiber.

The camera portion 500 is a digital single-lens reflex camera for imaging the fundus image. The adapter 400 and the camera portion 500 are connected to each other via a general-purpose camera mount, so the adapter 400 and the camera portion 500 are easily attachable to and detachable from each other.

The fundus image is formed on a surface of an area sensor 501.

Figure 9:
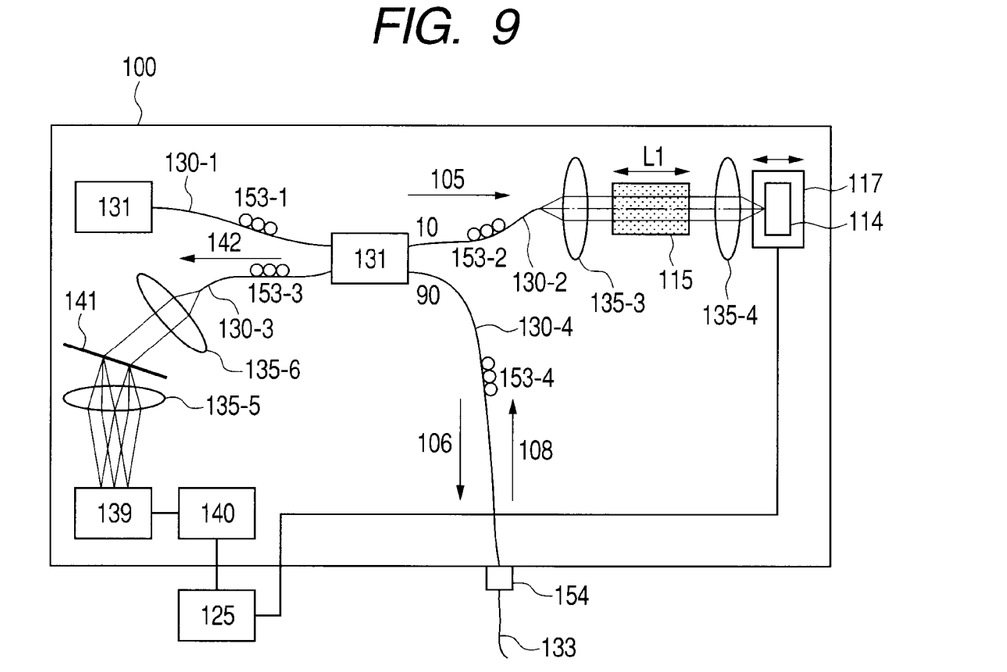
FIG. 9 is a diagram illustrating a structure of an OCT imaging portion of the OCT apparatus according to Embodiment 2 of the present invention.

In this example, the OCT imaging portion 100 has a structure in which a part of the optical system is constituted of an optical fiber for downsizing the apparatus.

The structure of this embodiment is basically the same as the structure of Embodiment 1 except for that the optical fiber is used for the optical path.

Next, a structure of the OCT imaging portion 100 is described.

FIG. 9 is a diagram illustrating the structure of the OCT imaging portion 100.

In FIG. 9, the OCT imaging portion 100 includes a light source 101, a reference beam 105, a measuring beam 106, a return beam 108, and a mirror 114.

The OCT imaging portion 100 further includes a dispersion compensation glass 115, an electrical stage 117, an optical coupler 131, lenses 135-3, 135-4, 135-5, and 135-6, a line camera 139, a frame grabber 140, single mode fibers 130-1, 130-2, 130-3, 130-4, and 133, a connector 154, and polarization controllers 153-1, 153-2, 153-3, and 153-4. A personal computer is represented by 125.

Next, a structure of the optical system of the OCT imaging portion 100 is described.

As illustrated in FIG. 9, the OCT imaging portion 100 constitutes a Michelson interferometer as a whole.

In FIG. 9, the light beam emitted from the light source 101 is split by the optical coupler 131 into the reference beam 105 and the measuring beam 106 at a ratio of 10:90. The measuring beam 106 is directed by the optical fiber 130-4 to the connector 154. After that, the light beam reaches the eye 107 to be inspected to be observed via the adapter 400 and the fundus camera main body portion 300 (FIG. 8).

Further, the measuring beam 106 is reflected or scattered by the eye 107 to be inspected so as to return as the return beams 108, which is combined with the reference beam 105 by the optical coupler 131. After the reference beam 105 and the return beams 108 are combined, the beam enters the line camera 139. The obtained light intensity is used for constituting the tomographic image of the eye 107 to be inspected.

Next, a periphery of the light source 101 is described.

The light source 101 is a super luminescent diode (SLD) that is a typical low coherence light source, which is the same as the light source 101 in Embodiment 1, so description thereof is omitted.

The light beam emitted from the light source 101 is directed through the single mode fiber 130-1 to the optical coupler 131 and is split at an intensity ratio of 90:10, so as to make the measuring beam 106 and the reference beam 105, respectively.

Next, the optical path of the reference beam 105 is described.

The reference beam 105 split by the optical coupler 131 is directed through the single mode fiber 130-2 to the lens 135-3 and is adjusted to be a parallel beam having a beam diameter of 1 mm.

Next, the reference beam 105 is condensed by the lens 135-4 and is reflected by the mirror 114 to be directed to the optical coupler 131 again.

Here, the dispersion compensation glass 115 through which the reference beam 105 passes is used for compensating for the dispersion of the measuring beam 106 when the measuring beam 106 enters the eye 107 to be inspected and is reflected thereby, with respect to the reference beam 105.

The dispersion compensation glass 115 has a length L1. In this example, L1=23 mm, which is a diameter assumed for a Japanese average eyeball.

Further, an electrical stage 117 may move in the direction indicated by the arrow, so that the optical path length of the reference beam 105 may be adjusted and controlled.

In addition, the electrical stage 117 is controlled by the personal computer 125, which is characteristic of the present invention.

Next, the optical path of the measuring beam 106 is described.

The measuring beam 106 split by the optical coupler 131 is directed through the single mode fiber 130-4 to the connector 154.

After that, the measuring beam 106 is directed to the retina of the eye 107 to be inspected via the optical fiber 133, the connector 410, the adapter 400, and the fundus camera main body portion 300 (FIG. 8).

When the measuring beam 106 enters the eye 107 to be inspected, the beam is reflected or scattered by the retina 127 so as to become the return beams 108.

The return beams 108 is directed again to the optical coupler 131 via the fundus camera main body portion 300, the adapter 400, the connector 410, the single mode fiber 133, and the connector 154 in this order.

The reference beam 105 and the return beams 108 described above are combined by the optical coupler 131 to be further split at a ratio of 90:10.

Then, the combined light beam 142 is spectrally processed by the transmission grating 141 for each wavelength and is condensed by the lens 135-5, and then the line camera 139 converts the light intensity for each position (wavelength) into a voltage.

Specifically, an interference pattern of the spectrum region on the wavelength axis is observed by the line camera 139.

The obtained voltage signals are converted into digital values by the frame grabber 140, and the digital values are supplied to the personal computer 125, which performs data processing so as to form the tomographic image.

Here, the line camera 139 has 1,024 pixels and may obtain intensity of the combined light beam 142 for each wavelength (1,024 splits).

The structure of the measurement system of the OCT apparatus according to this embodiment is substantially the same as that of Embodiment 1, so description thereof is omitted.

In addition, the method of obtaining the tomographic image by using the OCT apparatus according to this embodiment is also substantially the same as that of Embodiment 1, so detailed description thereof is omitted.

The OCT apparatus 200 controls the XY scanner 408, and the line camera 139 obtains the interference pattern, with the result that the tomographic image of the retina 127 may be obtained (FIG. 8).

In addition, the method of obtaining the three-dimensional image by using the OCT apparatus, which is characteristic of the present invention, is also substantially the same as that of Embodiment 1, so detailed description thereof is omitted.

Here, the mirror 114 as the reference mirror and the focus lens 304 for adjusting the focal position are controlled respectively, with the result that the tomographic image of the retina 127 and the three-dimensional image constituted of the plurality of tomographic images may be obtained (FIGS. 8 and 9).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-331805, filed Dec. 26, 2008, which is hereby incorporated by reference herein in its entirety.

The invention claimed is:

1. An optical tomographic imaging apparatus acquiring a tomographic image of an object based on combined light of return light from the object irradiated with measuring light and reference light corresponding to the measuring light, comprising:
   a position information acquiring unit that acquires three-dimensional positional information of a specific position of the object in a depth direction from a plurality of tomographic images of the object;
   a control unit that controls a focusing unit to change the position of the focusing unit along an optical axis of the measuring light based on the acquired three-dimensional positional information.

2. The optical tomographic imaging apparatus according to claim 1, wherein the position information acquiring unit acquires the three-dimensional positional information from two or more cross sections that cross each other.

3. The optical tomographic imaging apparatus according to claim 2, further comprising a scanning unit that scans the measuring light on the object,
   wherein the control unit controls the focusing unit and the scanning unit to change the position of the focusing unit while scanning the measuring light.

4. The optical tomographic imaging apparatus according to claim 3,
   wherein the position information acquiring unit acquires information on a three-dimensional plane as the three-dimensional positional information, from two or more cross sections that cross each other, and
   wherein the control unit controls the focusing unit and the scanning unit to change the position of the focusing unit while scanning the measuring light, along the three-dimensional plane.

5. The optical tomographic imaging apparatus according to claim 3, further comprising an optical path length difference adjustment unit that adjusts an optical path length difference between an optical path length of the measuring light and an optical path length of the reference light,
   wherein the control unit controls the focusing unit and the scanning unit to change, while scanning the measuring light, the position of the focusing unit in a direction along an optical axis of the measuring light and the optical path length difference based on the acquired three-dimensional positional information.

6. The optical tomographic imaging apparatus according to claim 5, further comprising an imaging unit that acquires an image of the specific position after the position of the focusing unit in the direction along the optical axis of the measuring light and the optical path length difference are changed.

7. The optical tomographic imaging apparatus according to claim 1, wherein the object is an eye, the specific position is a specific layer of a retina of the eye.

8. The optical tomographic imaging apparatus according to claim 7, wherein the specific layer of the retina is a retinal pigment epithelial layer.

9. The optical tomographic imaging apparatus according to claim 7, wherein the specific layer of the retina is a retinal nerve fiber layer.

10. The optical tomographic imaging apparatus according to claim 7, further comprising a fundus camera main body portion in the optical tomographic imaging apparatus for imaging a tomographic image of a fundus of an eye, and a camera portion for imaging a surface image of the fundus of the eye.

11. The optical tomographic imaging apparatus according to claim 1, wherein the tomographic image is acquired by a Fourier-domain method.

12. The optical tomographic imaging apparatus according to claim 1, further comprising:
   a beam splitter that splits a light beam from a light source into the measuring light and the reference light;
   optical paths through which the measuring light is directed to the object and the reference light is directed to a reference mirror; and
   an imaging device that uses the return light of the measuring beam light that is reflected or scattered by the object and the reference light reflected by the reference mirror to take the tomographic image of the object.

13. An optical tomographic imaging method acquiring a tomographic image of an object based on a combined light of a return light from the object irradiated with a measuring light and a reference light corresponding to the measuring light, comprising:
   acquiring three-dimensional positional information of a specific position of the object in a depth direction from a plurality of tomo graphic images of the object; and
   changing the position of a focusing unit along an optical axis of the measuring light based on the acquired three-dimensional positional information.

14. The optical tomographic imaging method according to claim 13, wherein
   the three-dimensional positional information is acquired from two or more cross sections that cross each other.

15. The optical tomographic imaging apparatus method according to claim 13, wherein:
   the object is an eye; and
   the specific position is a specific layer of a retina of the eye.

16. A computer-readable storage medium storing a program for causing a computer to execute the optical tomographic imaging method according to claim 13.

* * * * *